United States Patent
Artenstein (10) Patent No.: US 7,265,256 B2
(45) Date of Patent: Sep. 4, 2007

(54) BANDAGING DEVICE FOR SEQUESTERING A WOUND OR INOCULATION SITE

(75) Inventor: Andrew W. Artenstein, Pawtucket, RI (US)

(73) Assignee: Ther Memorial Hospital, Pawtucket, RI (US)

( * ) Notice: Subject to any disclaimer, the term of this patent is extended or adjusted under 35 U.S.C. 154(b) by 164 days.

(21) Appl. No.: 10/741,531

(22) Filed: Dec. 19, 2003

(65) Prior Publication Data

US 2004/0143202 A1     Jul. 22, 2004

Related U.S. Application Data

(60) Provisional application No. 60/441,409, filed on Jan. 17, 2003.

(51) Int. Cl.
*A61F 13/00* (2006.01)
(52) U.S. Cl. ............................ 602/42; 602/54; 602/58; 128/888
(58) Field of Classification Search ............ 602/41–44, 602/48, 57–59; 604/304–308; 128/888, 128/889; D24/189
See application file for complete search history.

(56) References Cited

U.S. PATENT DOCUMENTS

| | | |
|---|---|---|
| 679,918 A | 8/1901 | Shears |
| 697,637 A | 4/1902 | Lee |
| 720,812 A | 2/1903 | Johnson |
| 2,221,758 A | 11/1940 | Elmquist |
| 2,367,690 A | 1/1945 | Purdy |
| 2,443,140 A | 6/1948 | Larsen |
| 3,026,874 A | 3/1962 | Stevens |
| 4,285,338 A | 8/1981 | Lemelson |
| 4,399,816 A | 8/1983 | Spangler |
| 4,667,666 A | 5/1987 | Fryslier |
| 4,726,364 A | 2/1988 | Wylan |

(Continued)

FOREIGN PATENT DOCUMENTS

DE     29820217 U1     5/1999

(Continued)

OTHER PUBLICATIONS

3M TM Microfoam TM Sugical Tape and Sterile Tape Patch.*

(Continued)

*Primary Examiner*—Kim M. Lewis
(74) *Attorney, Agent, or Firm*—Hamilton, Brook, Smith & Reynolds, P.C.

(57) ABSTRACT

A bandaging device and method for sequestering a wound or an inoculation site on a patient are provided. The device comprises a body integrally formed to encase the wound or inoculation site. The formed body comprises a substantially transparent top portion for visually inspecting the wound or inoculation site, a side portion descending from the top portion to a lower edge, and a flange extending radially outward from the lower edge. The bandaging device is formed from a material that is substantially liquid-impermeable to prevent liquid or other contaminants from reaching the wound or inoculation site. The bandaging device also comprises at least one section that is formed from a material that is substantially liquid-impermeable and vapor-permeable to allow vapor to reach the wound or inoculation site while preventing liquid or other contaminants from contacting therewith.

31 Claims, 4 Drawing Sheets

U.S. PATENT DOCUMENTS

| | | |
|---|---|---|
| 4,754,750 A | 7/1988 | Imonti |
| 4,870,977 A | 10/1989 | Imonti |
| 4,905,681 A | 3/1990 | Glascock |
| 4,907,579 A | 3/1990 | Kum |
| 4,917,112 A * | 4/1990 | Kalt .......................... 602/58 |
| 4,972,829 A | 11/1990 | Knerr |
| 5,000,741 A | 3/1991 | Kalt |
| 5,032,103 A | 7/1991 | Larsson |
| 5,060,662 A | 10/1991 | Farnswoth, III |
| 5,062,433 A | 11/1991 | Kummer |
| 5,109,874 A | 5/1992 | Bellingham et al. |
| 5,144,958 A | 9/1992 | Krueger et al. |
| 5,395,675 A | 3/1995 | Altholz et al. |
| 5,487,889 A | 1/1996 | Eckert et al. |
| 5,580,346 A | 12/1996 | Spier |
| 5,817,145 A | 10/1998 | Augustine et al. |
| 5,876,365 A | 3/1999 | Hart |
| 6,005,159 A | 12/1999 | Spier |
| 6,041,786 A | 3/2000 | DeLaTorre |
| 6,066,773 A | 5/2000 | Freeman |
| 6,096,943 A | 8/2000 | Maiwald |
| 6,107,536 A | 8/2000 | Dadinis |
| 6,110,197 A * | 8/2000 | Augustine et al. .......... 607/108 |
| 6,143,945 A | 11/2000 | Augustine et al. |
| 6,274,787 B1 * | 8/2001 | Downing .................... 602/41 |
| 6,343,604 B1 | 2/2002 | Beall |
| 2002/0029010 A1 | 3/2002 | Augustine et al. |
| 2003/0009122 A1 | 1/2003 | Veras |

FOREIGN PATENT DOCUMENTS

| | | | |
|---|---|---|---|
| GB | 2082919 A | * | 3/1982 |
| GB | 2223410 A | | 4/1990 |

OTHER PUBLICATIONS

STML Dressings Datacard.*

* cited by examiner

BANDAGING DEVICE FOR SEQUESTERING A WOUND OR INOCULATION SITE

RELATED APPLICATION

This application claims the benefit of U.S. Provisional Application No. 60/441,409, filed Jan. 17, 2003, the entire teachings of which are incorporated herein by reference.

BACKGROUND OF THE INVENTION

Depending upon the nature of a wound or inoculation site, it may be desirable to protect or sequester the site until it can heal. Bandaging devices are used to promote healing and prevent infection. For communicable diseases, a bandaging device on a communicable lesion may be desirable to prevent contamination to oneself and others. A means for ensuring that a wound or inoculation site can heal promptly and in a safe manner is desirable.

SUMMARY OF THE INVENTION

The invention pertains to a bandaging device for sequestering a wound or an inoculation site on a patient. The device comprises a body integrally formed to encase the wound or inoculation site. The formed body can include a substantially transparent top portion for visually inspecting the wound or inoculation site, a side portion descending from the top portion to a lower edge, and a flange extending radially outward from the lower edge. The bandaging device can be formed from a material that is substantially liquid-impermeable to prevent liquid or other contaminants from reaching the wound or inoculation site. Beneficially, the substantially liquid-impermeable material prevents egress of viruses or other micro-organisms, if present at the inoculation site or wound, to an external surface of the bandaging device. The bandaging device also comprises at least one section that is formed from a material that is substantially liquid-impermeable and vapor-permeable to allow vapor to reach the wound or inoculation site while preventing liquid or other contaminants from contacting therewith.

In a particular embodiment, at least one window or region formed from the material that is substantially liquid-impermeable and vapor-permeable is provided to allow vapor to pass therethrough. The material that forms the window(s) or region(s) of the bandaging device can include polypropylene, such as spun-bonded polypropylene.

In one embodiment, a medical grade adhesive can be attached to an underside of the flange for attaching the bandaging device to the skin of the patient. In other embodiments, the underside of the flange is attachable to a bandaging material that is affixable to the skin of the patient. An adhesive can be used to attach the bandaging material to the skin of the patient. In further embodiments, the underside of the flange can be attached to the material that is substantially liquid-impermeable and vapor-permeable. A washer can be attached to the material that is substantially liquid-impermeable and vapor-permeable. The washer can be attached to a bandaging material that can be affixed to the skin of the patient. A release layer can be disposed on the adhesive during storage of the bandaging device.

In other embodiments, a medical grade adhesive washer can be attached to an underside of the flange for attaching the bandaging device to the skin of the patient. In particular embodiments, the washer can include an open or closed cell foam washer. A release layer can be disposed on the washer prior to being attached to the skin of the patient. In other embodiments, a washer can be disposed within the body adjacent the bandaging material. An antibacterial medication can be disposed on an interior surface of the side portion to provide the antibacterial medication adjacent to the wound or inoculation site. In a particular embodiment, the side portion of the bandaging device extends perpendicularly away from the skin of the patient when the bandaging device is disposed thereon, and the flange extends perpendicularly away from the side portion.

In one embodiment, the body of the bandaging device can include polyester, polyethylene terephthalate glycol, styrene, polyvinyl chloride, or combinations thereof. The bandaging device can be configured to encase lesions, inoculation sites, burns, warts, infectious lesions, skin cancers, wounds and suture sites. The bandaging device can be sealed within a blister pack.

A bandaging device for sequestering a wound or inoculation site on a patient in need thereof in accordance with another embodiment of the present invention comprises a flange, a side portion extending from the flange, and a substantially transparent top portion supported by the side portion. The bandaging device can be formed from a material that is substantially liquid-impermeable and vapor-impermeable except at least one window or region that is formed in the bandaging device from a material that is substantially liquid-impermeable and vapor-permeable to allow vapor to reach a wound or inoculation site on the patient while preventing liquid or other contaminants from contacting therewith.

This invention also pertains to methods for sequestering a wound or inoculation site on a patient in need thereof by encasing the wound or inoculation site with a bandaging device having a body integrally formed to encase the wound or inoculation site. The formed body comprises a substantially transparent top portion for visually inspecting the wound or inoculation site, a side portion descending from the top portion to a lower edge, and a flange extending radially outward from the lower edge. The bandaging device can be formed from a material that is substantially liquid-impermeable to prevent liquid or other contaminants from reaching the wound or inoculation site. The bandaging device also comprises at least one section that is formed from a material that is substantially liquid-impermeable and vapor-permeable to allow vapor to reach the wound or inoculation site while preventing liquid or other contaminants from contacting therewith. The wound or inoculation site is encased by fixably attaching the bandaging device to the skin of the patient. The wound or inoculation site can be visually inspected through the top portion. In a particular embodiment, the flange is attachable to a bandaging material that is attachable to the skin of the patient.

In further embodiments, a bandaging device for sequestering a wound or inoculation site on a patient in need thereof comprises a body integrally formed to encase the wound or inoculation site. The body comprises at least one section that is substantially transparent for visually inspecting the wound or inoculation site. The body is at least partially arcuate from a top portion to a lower edge from which a flange extends radially outward, and can be formed from a material that is substantially liquid-impermeable to prevent liquid or other contaminants from reaching the wound or inoculation site. The bandaging device can also include at least one section that is formed from a material that is substantially liquid-impermeable and vapor-permeable to allow vapor to reach the wound or inoculation site while preventing liquid or other contaminants from contacting therewith. In a particular embodiment, at least one window or region is provided in the bandaging device to allow vapor to pass therethrough, wherein the window or region is formed from the material that is substantially liquid-impermeable and vapor-permeable.

Thus, in accordance with aspects of the present invention, a bandaging device is provided which allows the visual inspection of the wound or inoculation site without removing the device from the patient. This allows convenient monitoring of the wound or inoculation site without changing the bandage or potentially exposing people, including the patient, to contaminated materials. The bandaging device beneficially prevents the patient from itching/touching the wound or inoculation site. Since the top portion of the bandaging device is supported above the wound or inoculation site, the bandaging device does not become contaminated. The bandaging device in accordance with embodiments of the invention allows vapor or airflow to the wound or inoculation site, which may increase the healing process while preventing liquid, such as water, or other contaminants from contacting the wound or inoculation site. The patient can thus bathe and shower without getting the wound or inoculation site wet, which could macerate the wound or inoculation site and slow down the healing process.

BRIEF DESCRIPTION OF THE DRAWINGS

The foregoing and other objects, features and advantages of the invention will be apparent from the following more particular description of embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of various embodiments of the invention follows.

Figure 1:
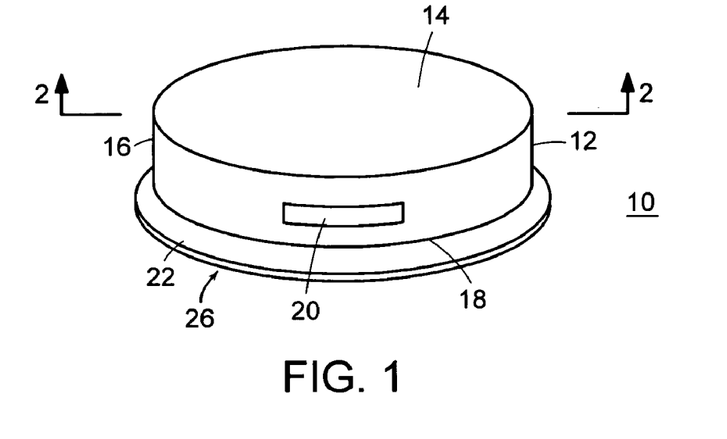
FIG. 1 is a perspective view of a bandaging device in accordance with an embodiment of the present application.
Figure 2:
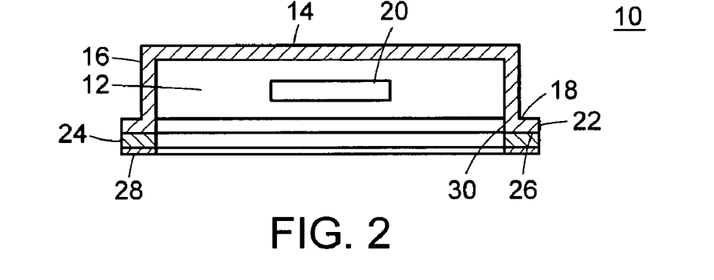
FIG. 2 is a cross-sectional view of the bandaging device of FIG. 1 taken along line 2-2.
Figure 3:
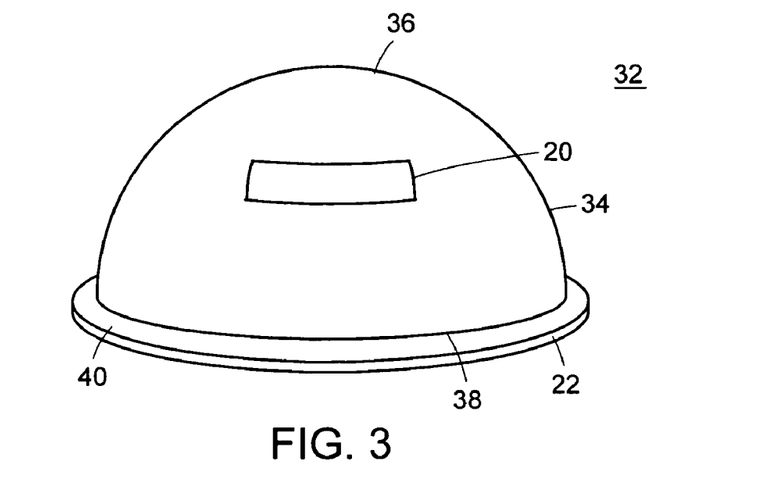
FIG. 3 is a perspective view of a bandaging device in accordance with an alternative embodiment of the present invention.
Figure 4:
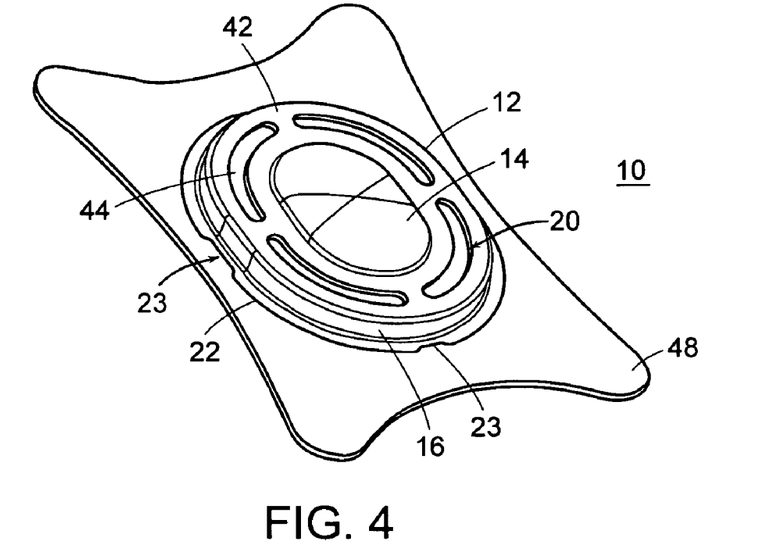
FIG. 4 is a perspective view of a bandaging device in accordance with a further embodiment of the present invention.
Figure 5:
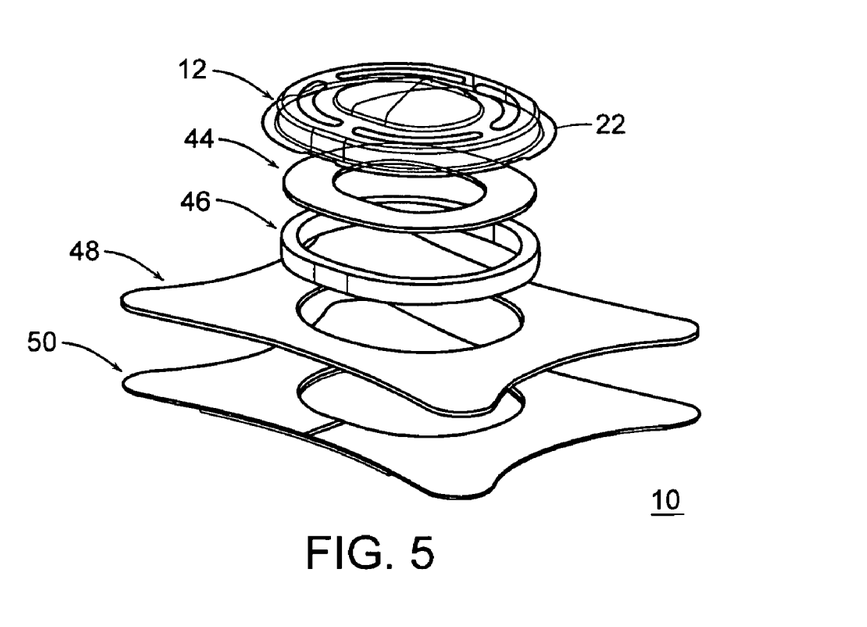
FIG. 5 is an exploded view of the bandaging device illustrated in FIG. 4.
Figure 6:
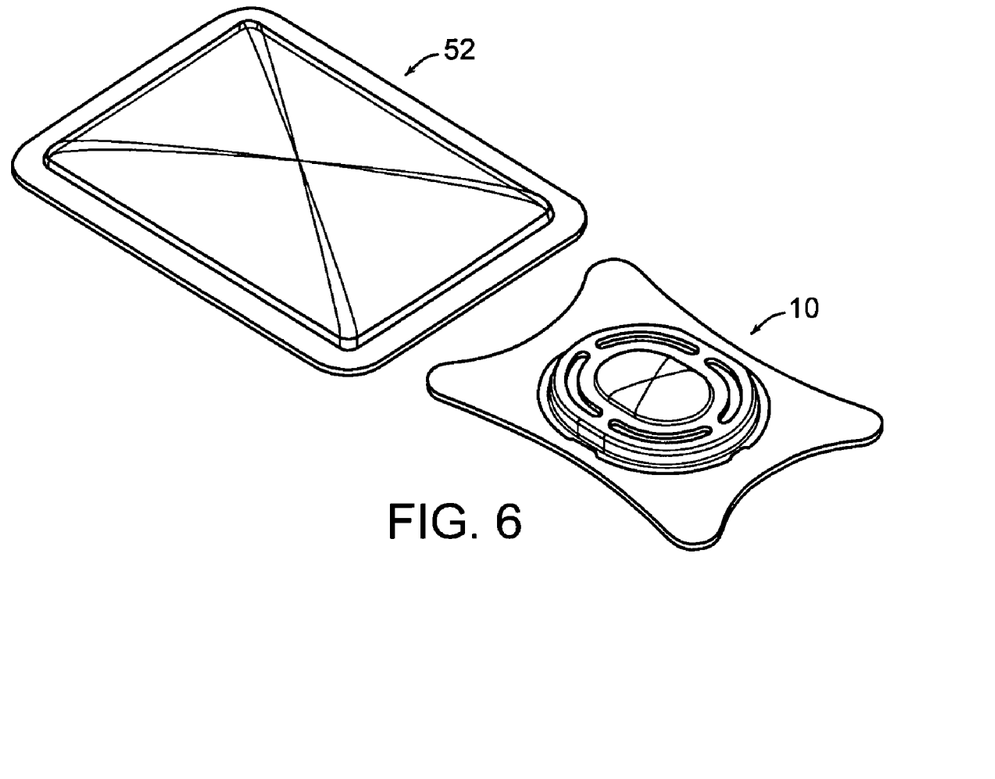
FIG. 6 is a perspective view of a bandaging device and an exemplary blister pack.
Figure 7:
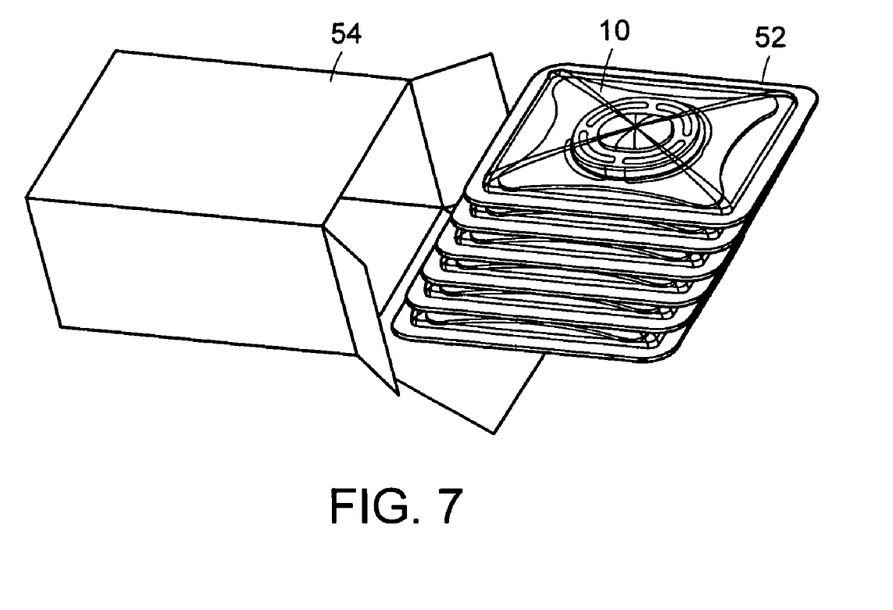
FIG. 7 is a perspective view of a plurality of bandaging devices enclosed within individual blister packs being inserted into a container.
Figure 8:
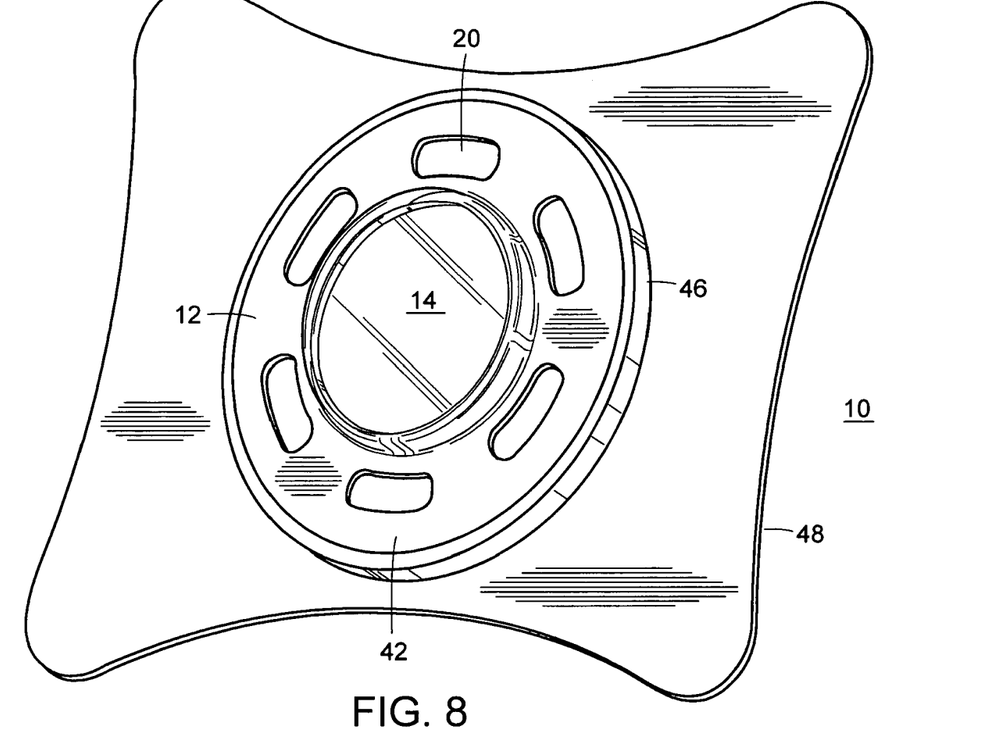
FIG. 8 is a perspective view of a bandaging device in accordance with yet another embodiment of the present invention.
Figure 9:
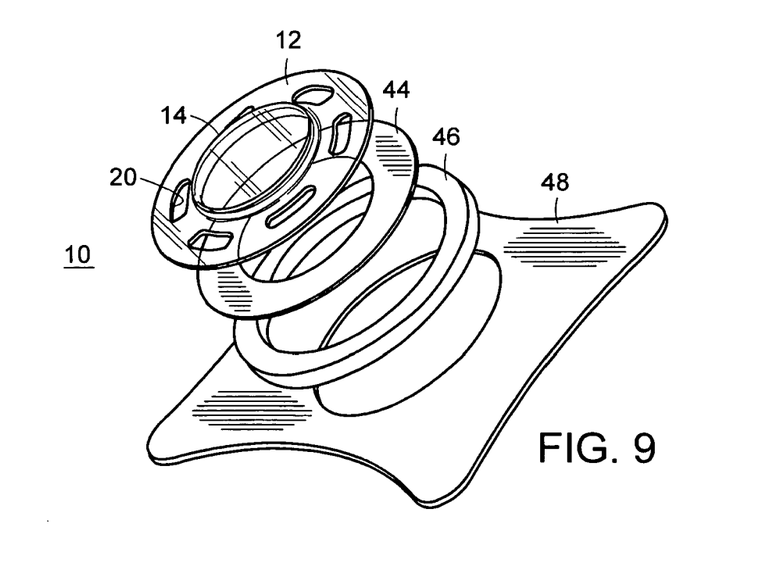
FIG. 9 is an exploded view of the bandaging device illustrated in FIG. 8.

An embodiment of a bandaging device for sequestering, for example, wounds, inoculation sites, lesions, burns, warts, infectious lesions, skin cancers, suture sites, or other suitable areas of a patient is illustrated in FIGS. 1 and 2. In this embodiment, a body 12 is integrally formed, i.e., a single-piece construction with no joints. The body 12 comprises a substantially transparent top portion 14 through which the condition of the wound or inoculation site can be inspected. This is especially desirable for a smallpox vaccine site, for example, where a "take" is determined by its appearance. A "take" is defined as a reaction at the inoculation site, typically demonstrated by scabby blisters surrounded by a halo of red, indicating that the patient is mounting an immune response. In this embodiment, the top portion 14 and body 12 are circular, although they can be any shape such as oval, partially oval, square, elongate, triangle, domed, semi-hemispherical (bubble-shaped), etc.

The bandaging device 10 is formed, in one embodiment, from a material that is liquid-impermeable to prevent liquid or other contaminants from contacting or leaving the wound or inoculation site. For example, the bandaging device 10 can be formed from polyester, polyethylene terephthalate glycol, styrene, polyvinyl chloride, or other suitable materials. In an alternative embodiment, the bandaging device 10 is formed from at least a first material that is not liquid impermeable and a second material that is hydrophobic such that the device 10 is liquid impermeable. The impermeable nature of the device 10 prevents exudate from leaving the sequestered site.

Descending from the top portion 14 is a side portion 16 that extends to a lower edge 18. In one embodiment, the side portion or wall 16 is substantially perpendicular relative to the skin of the patient. The side portion 16 supports the top portion 14 above the wound or inoculation site and thus prevents the top portion 14 from contacting the wound or inoculation site to prevent irritation and breakage or disruption of the scabbing process. The side portion 16 is of a suitable dimension such that the bandaging device 10 extends above the wound or inoculation site. In one embodiment, the bandaging device 10 is configured to contact the patient's skin around the wound or inoculation site to encase the same while including a raised portion suspended above the wound or inoculation site.

To provide airflow to the wound or inoculation site in this embodiment, at least one window, vent, or region 20 is provided. It is known that oxygen helps a wound to heal faster. In this embodiment, one or more windows can be provided in the side portion 16. A material that is substantially liquid-impermeable, i.e., hydrophobic, and vapor-permeable can be affixed to the window 20 to prevent a "greenhouse" effect at the wound or inoculation site. That is, without airflow to the wound, bacteria or other undesirable substances may be contained within the bandaging device which could result in wound infection. An advantage of putting one or more windows 20 in the side portion 16 is that the material that forms the windows does not need to be substantially transparent. Another advantage of putting the windows 20 in the side portion 16 is to facilitate maximum airflow to the wound or inoculation site. For example, opposed windows 20 in the side 16 provide an airflow path, i.e., cross-ventilation, through the bandaging device 10. Thus, when the device 10 is attached to an arm of a patient, for example, the natural movement of the arm forces air through the device 10 to maximize airflow to the wound or inoculation site. It has been found that windows 20 provided on or adjacent the top portion 14 provide sufficient airflow to the wound or inoculation site.

In a particular embodiment, a spun-bonded polypropylene or other suitable materials can be used to form the window 20. In alternative embodiments, a cloth-type material can be provided in the window 20. This airflow enhancement allows the wound or inoculation site to breathe, facilitates drying of the lesion or wound, and helps prevent maceration that can lead to secondary infection of lesions. The pores of the material should be suitable for airflow but should prevent leaking/seepage of the exudate or prevent liquids or other contaminants from entering into the wound site.

A flange 22 for attaching the bandaging device 10 to the skin of the patient extends radially outward from the lower edge 18. In a particular embodiment, the flange 22 can extend perpendicularly away from the side portion 16, i.e., parallel to the patient's skin. In one embodiment, the bandaging device 10 is a single-piece, integrally formed construction to optimize the integrity of the device as it pertains to containment of infectious materials and to maximize the simplicity of use for non-medical persons, e.g., the device can be put on, changed, and removed with ease.

To affix the bandaging device 10 to the skin of a patient in one embodiment, a medical grade adhesive 24 can be provided on an underside 26 of the flange 22. Medical grade adhesives are defined as being non-sensitizing, non-irritating and nontoxic for skin contact applications. The adhesive fixably attaches the bandaging device 10 to the skin under normal conditions, but is sufficiently releasable so that the device can be easily removed without hurting the patient's skin. A release layer 28 can be provided on the adhesive 24 during storage of the bandaging device. In other embodiments, a medical grade washer, which can be formed from open or closed cell foam, can be attached to the underside 26 of the flange 22. A closed cell washer can be used in applications where it is desirable that the washer repel and not absorb any liquid(s) present at the inoculation site or wound. An open cell washer can be used in applications where it is desirable to absorb liquid(s) present at the inoculation site or wound. A release layer can be provided on the washer prior to being attached to the skin of the patient.

In further embodiments, an antibacterial medication can be provided on at least a portion of an interior surface 30 of the side portion 16 to provide antibacterial medication adjacent to the wound or inoculation site. In other embodiments, an antibacterial medication can be provided on an inner portion of the washer to provide antibacterial medication adjacent to the wound or inoculation site.

FIG. 3 illustrates another embodiment of a bandaging device 32 in accordance with aspects of the present invention. In this embodiment, a body 34 is at least partially arcuate from a top portion 36 to a lower edge 38 from which a flange 40 extends radially outward. At least a portion or section of the body 34 is substantially transparent such that the wound or inoculation site can be viewed. The bandaging device 32 can be formed from a material that is liquid-impermeable to prevent liquid or other contaminants from contacting the wound or inoculation site. One or more windows, vents, or regions 20 can be provided to provide airflow to the wound or inoculation site while preventing liquids from entering the site.

FIGS. 4 and 5 illustrate a further embodiment of a bandaging device 10. In this embodiment, the body 12 includes an oblong, bubble-shaped top portion 14. In one embodiment, the body 12 is formed from polyethylene terephthalate glycol (PETG) and has a thickness of about 0.2 mm (0.008 inches).

One or more vents or windows 20 can be provided in a region 42 adjacent the top portion 14. A material 44 that is substantially liquid impermeable and vapor-permeable can be placed or affixed to the underside of region 42 to allow airflow through the windows 20 while preventing liquid or other contaminants from passing therethrough for the reasons described above. In a particular embodiment, the material 44 includes polypropylene that is marketed by Kimberly-Clark Corporation as SPUNGUARD® wrap.

In a particular embodiment, an optional washer 46, such as an open or closed cell foam washer, can be provided adjacent to the material 44. The washer 46 can be of varying heights in specific embodiments. The washer 46 can help contain the exudate, bacteria, viruses, etc. from leaving the sequestered site and provides a shock absorber when the body 12 is bumped against a surface. In one embodiment, the washer 46 includes closed cell polyethylene that is coated on both sides with a pressure sensitive adhesive.

In one embodiment, the body 12 includes a flange 22 that can be attached to a bandaging material 48 that is affixed to the skin of the patient around the site to be sequestered. A pressure sensitive adhesive can be provided on the bottom side of the bandaging material 48. A release liner 50 can be provided on the adhesive prior to use. In a particular embodiment, the release liner 50 can include tabs or non-adhesive portions that allow the individual applying the bandaging device 10 to easily manipulate the device by holding the tabs while attaching the bandaging material 48 to the patient's skin.

In other embodiments, the body 12 is affixed to the bandaging material 48 by material 44 and washer 46. In further embodiments, the flange 22 can be directly attached to the patient's skin, thereby obviating the need for the bandaging material 48. The flange 22 can include notches 23 to facilitate bending of the body 12. In a particular embodiment, the bandaging material 48 can include a spunlaced nonwoven polyester, such as SONTARA® fabric available from E. I. du Pont de Nemours and Company, polyethylene, or other suitable materials.

FIG. 6 illustrates an embodiment for packaging a single bandaging device 10. The device 10 can be hermetically sealed within a sealed package or pouch 52, such as a blister pack, which can be formed at least in part from TYVEK® material available from E. I. du Pont de Nemours and Company. As illustrated in FIG. 7, a plurality of bandaging devices 10 sealed within respective blister packs 52 can be included within a container 54.

FIGS. 8 and 9 illustrate another embodiment of a bandaging device 10. In this embodiment, the top portion 14 is raised above region 42 in which the windows 20 are provided. A material 44 that is substantially liquid impermeable and vapor-permeable is placed or affixed to the underside of region 42 to allow airflow through the windows 20 while preventing liquid or other contaminants from passing therethrough for the reasons described above. An optional washer 46 can be attached to the material 44 and bandaging material 48 to affix the body 12 to the bandaging material 48. In other embodiments, the body 12 can be attached directly to the bandaging material 48 or the patient's skin.

Embodiments of the present invention are particularly desirable for inoculation sites that are highly communicable such as smallpox. In the field of smallpox vaccinations, for example, a smallpox vaccine is uniquely administered by scarification at an inoculation site of the patient. A successful immune response is indicated by the development of a lesion at the inoculation site that evolves over time through stages that include blisters and scabs. The vaccine virus, which can include live *vaccinia* virus that is closely related to smallpox virus, is present in the lesion and discharges until the scab has separated from normal skin below. This process may not be complete for up to four weeks after vaccination.

During the period when the lesion is present, virus can be transmitted to other people who either come into contact with the lesion or with items, such as bandages, that have been in contact with the lesion. Additionally, a vaccinated patient may inadvertently contaminate other parts of the body by touching the contagious lesion.

Until now, inoculation sites, such as smallpox vaccination sites, have been covered with a small piece of gauze and held in place by an adhesive covering. There are numerous drawbacks to this approach, including the following: the lesion cannot be visualized without removing the bandage, thus potentially exposing people to contaminated materials; the gauze is in continual contact with the lesion and thus absorbs wound discharge and may cause maceration and slow down the healing process, and may contribute to secondary bacterial infections; viruses or other micro-organisms may escape from the wound or inoculation site to an external surface of the dressing; airflow is prevented, thus potentially further impeding the healing process; and the bandages are not water impermeable, making showering or bathing problematic.

Aspects of the present invention include features that mitigate some or all of the above drawbacks.

While this invention has been particularly shown and described with references to embodiments thereof, it will be understood by those skilled in the art that various changes in form and details may be made therein without departing from the scope of the invention encompassed by the appended claims.

What is claimed is:

1. A bandaging device for sequestering a wound or inoculation site on a patient in need thereof, the device including a single-piece body having no joints, the body being integrally formed to encase the wound or inoculation site, the body including at least one section that is substantially transparent for visually inspecting the wound or inoculation site, the body being at least partially arcuate from a top portion to a first lower edge from which a first flange extends radially outward and having a second portion descending from the top portion of the first flange to a second lower edge from which a second flange extends radially, the bandaging device being formed from a material that is substantially liquid-impermeable to prevent liquid or other contaminants from reaching the wound or inoculation site, the bandaging device also including at least one section that is located on the first flange formed from a material that is substantially liquid-impermeable and vapor-permeable to allow vapor to reach the wound or inoculation site while preventing liquid or other contaminants from contacting therewith.

2. The bandaging device of claim 1, wherein at least one section located on the first flange is provided in the bandaging device to allow vapor to pass therethrough, the window or region being formed from the material that is substantially liquid-impermeable and vapor-permeable.

3. The bandaging device of claim 1, wherein the bandaging device is configured to encase at least one of lesions, inoculation sites, burns, warts, infectious lesions, skin cancers, wounds and suture sites.

4. The bandaging device of claim 1, wherein the body is at least partially semi-hemispherical shaped.

5. The bandaging device of claim 1, further comprising a washer attached to an underside of the second flange for attaching the bandaging device to the skin of the patient.

6. The bandaging device of claim 1, wherein the bandaging device is sealed within a package.

7. A bandaging device for sequestering a wound or inoculation site on a patient in need thereof, comprising a single piece body having no joints, the body being integrally formed to encase the wound or inoculation site, the formed body having a substantially transparent top portion for visually inspecting the wound or inoculation site, a side portion descending from the top portion to a first lower edge, a first flange extending radially outward from the lower edge, and having a side portion descending from the top portion of the first flange to a second lower edge from which a second flange extends radially outward, the bandaging device being formed from a material that is substantially liquid-impermeable to prevent liquid or other contaminants from reaching the wound or inoculation site, the bandaging device also including at least one section located on the first flange that is formed from a material that is substantially liquid-impermeable and vapor-permeable to allow vapor to reach the wound or inoculation site while preventing liquid or other contaminants from contacting therewith.

8. The bandaging device of claim 7, wherein the material that is substantially liquid-impermeable and vapor-permeable comprises polypropylene.

9. The bandaging device of claim 8, wherein the polypropylene comprises spun-bonded polypropylene.

10. The bandaging device of claim 7, further comprising a medical grade adhesive attached to an underside of the second flange for attaching the bandaging device to the skin of the patient.

11. The bandaging device of claim 10, further comprising a release layer disposed on the adhesive during storage of the bandaging device.

12. The bandaging device of claim 7, further comprising a washer attached to an underside of the second flange for attaching the bandaging device to the skin of the patient.

13. The bandaging device of claim 12, further comprising an antibacterial medication disposed on an inner portion of the washer to provide the antibacterial medication adjacent to the wound or inoculation site.

14. The bandaging device of claim 12, wherein the washer includes an open cell foam.

15. The bandaging device of claim 12, wherein the washer includes a closed cell foam.

16. The bandaging device of claim 12, further comprising a release layer disposed on the washer prior to being attached to the skin of the patient.

17. The bandaging device of claim 7, wherein the body comprises polyester, polyethylene terephthalate glycol, styrene, polyvinyl chloride, or a combination thereof.

18. The bandaging device of claim 7, wherein an underside of the flange is attachable to a bandaging material that is affixable to the skin of the patient.

19. The bandaging device of claim 18, wherein an adhesive is used to attach the bandaging material to the skin of the patient.

20. The bandaging device of claim 18, wherein the bandaging material includes polyester, polyethylene, or a combination thereof.

21. The bandaging device of claim 18, further comprising a washer disposed within the body adjacent the bandaging material.

22. The bandaging device of claim 7, wherein the bandaging device is sealed within a package.

23. The bandaging device of claim 7, further comprising an antibacterial medication on an interior surface of the side portion to provide the antibacterial medication adjacent to the wound or inoculation site.

24. The bandaging device of claim 7, wherein the bandaging device is configured to encase at least one of lesions, inoculation sites, burns, warts, infectious lesions, skin cancers, wounds and suture sites.

25. The bandaging device of claim 7, further comprising providing at least one notch in the second flange to facilitate bending of the body.

26. A method for sequestering a wound or inoculation site on a patient in need thereof, comprising:
  a) providing a bandaging device having a single-piece body having no joints, the body being integrally formed to encase the wound or inoculation site, the formed body having a substantially transparent top portion for visually inspecting the wound or inoculation site, the body having a side portion descending from the top portion to a first lower edge, a first flange extending radially outward from the lower edge, and having a side portion descending from the top portion of the first flange to a second lower edge from which a second flange extends radially outward, the bandaging device being formed from a material that is substantially liquid-impermeable to prevent liquid or other contaminants from reaching the wound or inoculation site, the bandaging device also including at least one section located on the first flange that is formed from a material tat is substantially liquid-impermeable and vapor-permeable to allow vapor to reach the wound or inoculation site while preventing liquid or other contaminants from contacting therewith;
  b) encasing the wound or inoculation site by fixably attaching the bandaging device to the skin of the patient; and
  a) visually inspecting the wound or inoculation site through the top portion.

27. The method of claim 26, wherein the bandaging device is configured to encase at least one of lesions, inoculation sites, burns, warts, infectious lesions, skin cancers, wounds and suture sites.

28. The method of claim 26, further comprising an antibacterial medication on an interior surface of the side portion to provide the antibacterial medication adjacent to the wound or inoculation site.

29. The method of claim 26, wherein the bandaging device is configured to encase at least one of lesions, inoculation sites, burns, warts, infectious lesions, skin cancers, wounds and suture sites.

30. The method of claim 26, wherein the inoculation site is a smallpox inoculation site.

31. The method of claim 26, further comprising providing at least one notch in the flange to facilitate bending of die body.

* * * * *